United States Patent
He

(10) Patent No.: US 12,419,527 B2
(45) Date of Patent: Sep. 23, 2025

(54) COMPREHENSIVE WEARABLE VITAL SIGNS MONITOR

(71) Applicant: Verily Life Sciences LLC, South San Francisco, CA (US)

(72) Inventor: David He, San Mateo, CA (US)

(73) Assignee: Verily Life Sciences LLC, Dallas, TX (US)

( * ) Notice: Subject to any disclaimer, the term of this patent is extended or adjusted under 35 U.S.C. 154(b) by 357 days.

(21) Appl. No.: 17/946,582

(22) Filed: Sep. 16, 2022

(65) Prior Publication Data

US 2023/0095971 A1    Mar. 30, 2023

Related U.S. Application Data

(60) Provisional application No. 63/250,132, filed on Sep. 29, 2021.

(51) Int. Cl.
*A61B 5/0205* (2006.01)
*A61B 5/00* (2006.01)
(Continued)

(52) U.S. Cl.
CPC ...... *A61B 5/02055* (2013.01); *A61B 5/14551* (2013.01); *A61B 5/256* (2021.01);
(Continued)

(58) Field of Classification Search
CPC ............................ A61B 5/02055; A61B 5/305
(Continued)

(56) References Cited

U.S. PATENT DOCUMENTS 4,307,727 A    12/1981 Haynes
4,429,700 A    2/1984 Thees et al.
(Continued)

FOREIGN PATENT DOCUMENTS

CN    104203032 A    12/2014
DE    3713269 A1    12/1987
(Continued)

OTHER PUBLICATIONS

Gizdulich, P., et al., "Models of Brachial to Finger Pulse Wave Distortion and Pressure Decrement," Cardiovascular Research 33:698-705, 1997.
(Continued)

*Primary Examiner* — Nadia A Mahmood
(74) *Attorney, Agent, or Firm* — Christensen O'Connor Johnson Kindness PLLC

(57) ABSTRACT

A finger wearable device for monitoring vital signs at a finger includes a housing, a finger cuff, a plurality of vital sign sensors, and an electrocardiogram (ECG) sensor. The housing includes an interface surface for pressing against the finger. The finger cuff attaches to the housing and has a size and a shape to secure the housing to the finger and force the interface surface against the finger when the finger cuff is worn around the finger. The vital sign sensors are disposed in or on the housing and orientated to measure the vital signs from the finger of a wearer. The ECG sensor is disposed in or on the housing and coupled to first and second electrodes to measure ECG signals. The second electrode is disposed on the interface surface.

23 Claims, 6 Drawing Sheets

(51) Int. Cl.
*A61B 5/022* (2006.01)
*A61B 5/1455* (2006.01)
*A61B 5/256* (2021.01)
*A61B 5/282* (2021.01)
*A61B 5/305* (2021.01)
*A61B 5/021* (2006.01)
*A61B 5/024* (2006.01)
*A61B 5/08* (2006.01)

(52) U.S. Cl.
CPC .............. *A61B 5/282* (2021.01); *A61B 5/305* (2021.01); *A61B 5/6817* (2013.01); *A61B 5/6826* (2013.01); *A61B 5/6828* (2013.01); *A61B 5/6844* (2013.01); *A61B 5/021* (2013.01); *A61B 5/02241* (2013.01); *A61B 5/02416* (2013.01); *A61B 5/0816* (2013.01); *A61B 2562/0271* (2013.01)

(58) Field of Classification Search
USPC ........................................................ 600/301
See application file for complete search history.

(56) References Cited

U.S. PATENT DOCUMENTS

| | | | |
|---|---|---|---|
| 4,561,447 A | 12/1985 | Kawamura et al. | |
| 4,771,790 A | 9/1988 | Yamasawa et al. | |
| 4,821,734 A | 4/1989 | Koshino | |
| 4,966,156 A | 10/1990 | Perry et al. | |
| 5,107,848 A | 4/1992 | Oku | |
| 5,152,296 A | 10/1992 | Simons | |
| 5,218,966 A | 6/1993 | Yamasawa | |
| 5,351,694 A | 10/1994 | Davis et al. | |
| 6,280,390 B1 | 8/2001 | Akselrod et al. | |
| 6,336,044 B1 | 1/2002 | Ghiassi et al. | |
| 6,491,647 B1 | 12/2002 | Bridger et al. | |
| 6,533,729 B1 | 3/2003 | Khair et al. | |
| 6,537,271 B1 | 3/2003 | Murray et al. | |
| 6,669,648 B1 | 12/2003 | Fortin et al. | |
| 6,699,199 B2 | 3/2004 | Asada et al. | |
| 7,232,413 B2 | 6/2007 | Hashimoto et al. | |
| 7,306,563 B2 | 12/2007 | Huang | |
| 7,344,502 B2 | 3/2008 | Tanabe | |
| 7,674,231 B2 | 3/2010 | McCombie et al. | |
| 8,251,903 B2 | 8/2012 | LeBoeuf et al. | |
| 8,652,059 B2 | 2/2014 | Sano et al. | |
| 8,814,800 B2 | 8/2014 | Fortin et al. | |
| 8,959,745 B2 | 2/2015 | Ashida | |
| 9,345,424 B2 | 5/2016 | Wang et al. | |
| 9,480,423 B2 | 11/2016 | Kim et al. | |
| 9,554,484 B2 | 1/2017 | Rogers et al. | |
| 10,531,802 B2 | 1/2020 | Adi et al. | |
| 2002/0177781 A1 | 11/2002 | Amano | |
| 2002/0188206 A1 | 12/2002 | Davis et al. | |
| 2003/0163053 A1 | 8/2003 | Ogura et al. | |
| 2004/0044288 A1 | 3/2004 | Gorenberg et al. | |
| 2004/0077955 A1 | 4/2004 | Kawanishi et al. | |
| 2004/0116787 A1 | 6/2004 | Schnall | |
| 2004/0133081 A1* | 7/2004 | Teller ................... A61B 5/4884 600/595 |
| 2005/0096552 A1 | 5/2005 | Law et al. | |
| 2005/0215989 A1 | 9/2005 | Abboud et al. | |
| 2005/0228297 A1 | 10/2005 | Banet et al. | |
| 2005/0228298 A1 | 10/2005 | Banet et al. | |
| 2006/0161200 A1 | 7/2006 | Fallah | |
| 2006/0253041 A1 | 11/2006 | Shin et al. | |
| 2007/0118045 A1 | 5/2007 | Naghavi et al. | |
| 2007/0167844 A1 | 7/2007 | Asada et al. | |
| 2007/0203416 A1 | 8/2007 | Lowe | |
| 2008/0039731 A1 | 2/2008 | McCombie et al. | |
| 2008/0051667 A1* | 2/2008 | Goldreich ............... G16H 40/67 600/481 |
| 2008/0081963 A1 | 4/2008 | Naghavi et al. | |
| 2008/0171915 A1 | 7/2008 | Kawajiri et al. | |
| 2008/0214942 A1 | 9/2008 | Oh et al. | |
| 2008/0234788 A1 | 9/2008 | Wasowski | |
| 2009/0143655 A1 | 6/2009 | Shani | |
| 2009/0306487 A1 | 12/2009 | Crowe et al. | |
| 2010/0076331 A1* | 3/2010 | Chan ..................... A61B 5/681 600/509 |
| 2010/0106029 A1 | 4/2010 | Fraden | |
| 2010/0168531 A1 | 7/2010 | Shaltis et al. | |
| 2010/0286538 A1 | 11/2010 | Kim et al. | |
| 2011/0015504 A1 | 1/2011 | Yoo | |
| 2011/0054330 A1 | 3/2011 | Pfeiffer et al. | |
| 2012/0059267 A1 | 3/2012 | Lamego et al. | |
| 2012/0238887 A1 | 9/2012 | Gerdt et al. | |
| 2013/0144176 A1 | 6/2013 | Lee | |
| 2013/0317303 A1 | 11/2013 | Deshmukh et al. | |
| 2013/0345688 A1 | 12/2013 | Babkin et al. | |
| 2014/0114152 A1 | 4/2014 | Fournier | |
| 2014/0323891 A1 | 10/2014 | Sterling et al. | |
| 2015/0011906 A1 | 1/2015 | Wallach | |
| 2015/0080751 A1 | 3/2015 | Regh et al. | |
| 2015/0157247 A1 | 6/2015 | Weinstein et al. | |
| 2015/0272452 A1 | 10/2015 | Mullin et al. | |
| 2015/0272455 A1 | 10/2015 | Krasnov et al. | |
| 2015/0305632 A1 | 10/2015 | Najarian et al. | |
| 2015/0327784 A1 | 11/2015 | Lading et al. | |
| 2015/0366507 A1 | 12/2015 | Blank | |
| 2015/0374249 A1 | 12/2015 | Elliott et al. | |
| 2016/0113589 A1 | 4/2016 | Yoon | |
| 2016/0120420 A1 | 5/2016 | Liedl et al. | |
| 2016/0198955 A1 | 7/2016 | Fortin | |
| 2016/0317060 A1 | 11/2016 | Connor | |
| 2017/0055854 A1 | 3/2017 | Choucair et al. | |
| 2017/0135740 A1 | 5/2017 | Sara et al. | |
| 2017/0188975 A1 | 7/2017 | Banet et al. | |
| 2017/0238878 A1 | 8/2017 | Lading et al. | |
| 2017/0360306 A1 | 12/2017 | Narasimhan et al. | |
| 2017/0360313 A1 | 12/2017 | Baek et al. | |
| 2017/0367597 A1 | 12/2017 | Fortin | |
| 2018/0028777 A1 | 2/2018 | Cheng | |
| 2018/0046281 A1 | 2/2018 | Pi et al. | |
| 2018/0078154 A1 | 3/2018 | Knickerbocker et al. | |
| 2018/0078155 A1 | 3/2018 | Baek et al. | |
| 2018/0192900 A1 | 7/2018 | Wei | |
| 2018/0206746 A1 | 7/2018 | Narasimhan et al. | |
| 2018/0235468 A1 | 8/2018 | Khachaturian et al. | |
| 2018/0310835 A1 | 11/2018 | Sawanoi et al. | |
| 2019/0053723 A1 | 2/2019 | van Sparrentak et al. | |
| 2019/0104953 A1 | 4/2019 | Narasimhan | |
| 2019/0150765 A1 | 5/2019 | Fortin et al. | |
| 2019/0239787 A1 | 8/2019 | Pauley et al. | |
| 2020/0015689 A1 | 1/2020 | Allen et al. | |
| 2020/0060561 A1 | 2/2020 | DeBusschere et al. | |

FOREIGN PATENT DOCUMENTS

| | | |
|---|---|---|
| DE | 10 2015 103 261 | 1/2016 |
| EP | 0537383 A1 | 4/1993 |
| EP | 2319408 A1 | 11/2011 |
| JP | H634601 U | 5/1994 |
| JP | H08191779 A | 7/1996 |
| JP | H10295655 A | 11/1998 |
| JP | 2002010984 A | 1/2001 |
| JP | 2003245255 A | 9/2003 |
| JP | 2004305362 A | 11/2004 |
| JP | 2009213767 A | 9/2009 |
| JP | 2009284967 A | 12/2009 |
| JP | 2010284498 A | 10/2010 |
| JP | 2017047093 A | 3/2017 |
| WO | 2016/040256 A1 | 3/2016 |
| WO | 2016067866 A1 | 5/2016 |
| WO | 2018005298 A1 | 1/2018 |

OTHER PUBLICATIONS

Calhoon, J., "Tactile Sensors Support Next Generation Medical Devices," Aug. 25, 2016, <http://www.designworldonline.com/tactile-sensors-support-next-generation-medical devices/> [retrieved Jan. 18, 2017], 3 pages.

(56) References Cited

OTHER PUBLICATIONS

"The Finapres® Nova," FMS Finapres Medical Systems B.V., brochure, prior to Sep. 29, 2021, 4 pages.

Bogert, L.W.J., and J.J. van Lieshout, "Non-Invasive Pulsatile Arterial Pressure and Stroke Volume Changes From the Human Finger," Experimental Physiology 90.4:437-446, 2005.

Chen, C.-H., et al., "Estimation of Central Aortic Pressure Waveform by Mathematical Transformation of Radial Tonometry Pressure," Circulation 95:1827-1836, 1997.

Babbs, C.F., "Oscillometric Measurement of Systolic and Diastolic Blood Pressures Validated in a Physiologic Mathematical Model," BioMedical Engineering OnLine 11:56, Dec. 2012, pp. 1-22.

Baker, P.D., et al., "Theoretical Analysis of Non-Invasive Oscillometric Maximum Amplitude Algorithm for Estimating Mean Blood Pressure," Medical and Biological Engineering and Computing 35(3):271-278, May 1997.

Chen, S., et al., "Assessment of Algorithms for Oscillometric Blood Pressure Measurement," Proceedings of the International Instrumentation and Measurement Technology Conference (I2MTC 2009), Singapore, May 5-7, 2009, 5 pages.

"Continuous Noninvasive Arterial Pressure," Wikipedia, The Free Encyclopedia <https://en.wikipedia.org/wiki/Continuous_noninvasive_arterial_pressure?oldid+675060442>, prior to Sep. 29, 2021, 6 pages.

Da Fonseca, L.J.S., et al., "Radial Applanation Tonometry as an Adjuvant Tool in the Noninvasive Arterial Stiffness and Blood Pressure Assessment," World Journal of Cardiovascular Diseases 4(5):225-235, May 2014.

Digiglio, P., et al., "Microflotronic Arterial Tonometry for Continuous Wearable Non-Invasive Hemodynamic Monitoring," Annals of Biomedical Engineering 42(11):2278-2288, Nov. 2014.

Doshi, H., et al., "Does 'Hidden Undercuffing' Occur Among Obese Patients? Effect of Arm Sizes and Other Predictors of the Difference Between Wrist and Upper Arm Blood Pressures," Journal of Clinical Hypertension 12(2):82-88, Feb. 2010.

Drzewiecki, G., et al., "Theory of the Oscillometric Maximum and the Systolic and Diastolic Detection Ratios," Annals of Biomedical Engineering 22(1):88-96, Jan. 1994.

Drzewiecki, G.M., et al., "Arterial Tonometry: Review and Analysis," Journal of Biomechanics 16(2):141-152, 1983.

Forouzanfar, M., et al., "Ratio-Independent Blood Pressure Estimation by Modeling the Oscillometric Waveform Envelope," IEEE Transactions on Instrumentation and Measurement 63(10):2501-2503, Oct. 2014.

"High Blood Pressure," Statistical Fact Sheet, 2014 Update, American Heart Association, 2 pages.

"High Blood Pressure Facts," Centers for Disease Control and Prevention (CDC), Nov. 30, 2016 <https://www.cdc.gov/bloodpressure/facts.htm%5C>, 5 pages.

"Integrated Capacitive Pressure Sensors," Fraunhofer IMS, prior to Sep. 29, 2021, 2-page brochure.

"Invasive Blood Pressure," © Memscap, Mar. 23, 2018 <http://www.memscap.com/applications-and-market-segments/medical-and-biomedical/invasive-blood-pressure>, 1 page.

Jílek, J., and M. Štork, "The Effect of Wrist Cuff Width on Oscillometric Blood Pressure Waveforms," Electroscope, vol. 2008, No. III, 2008, 4 pages.

Jones, R.D.M., et al., "The Finapres 2300e Finger Cuff: The Influence of Cuff Application on the Accuracy of Blood Pressure Measurement," Anaesthesia 48(7):611-615, Jul. 1993.

Kountz, D.S., et al., "MD Mouse, a New Finger Blood Pressure Monitor, Consistently Underestimates Blood Pressure Compared to a Standard Automatic Syphygnomanometer," Abstract P-54, Journal of the American Society of Hypertension 9(4S):e35-e48, 2015.

Lan, H., et al., "Effect of Tissue Mechanical Properties on Cuff-Based Blood Pressure Measurements," Medical Engineering and Physics 33(10):1287-1292, Dec. 2011.

Lee, J., and K.C. Nam, "Tonometric Vascular Function Assessment," Chap. 30, in Barros de Mello (ed.), "Biomedical Engineering," Intech Europe, Rijeka, Croatia, 2009, pp. 549-566.

Lee, J., et al., "Comparison Between Dynamic Contour Tonometry and Goldmann Applanation Tonometry," Korean Journal of Ophthalmology 23(1):27-31, Mar. 2009.

Lee, J.Y., et al., "Blood Pressure Measurement Using Finger Cuff," Proceedings of the 27th Annual Conference of IEEE Engineering in Medicine and Biology, Shanghai, Sep. 1-4, 2005, 3 pages.

Liu, J., et al., "Patient-Specific Oscillometric Blood Pressure Measurement," IEEE Transactions on Biomedical Engineering 63(6):1220-1228, Jun. 2016.

Lyew, M.A., and J.W. Jamieson, "Blood Pressure Measurement Using Oscillometric Finger Cuffs in Children and Young Adults," Anaesthesia 49(10):895-899, Oct. 1994.

McEniery, C.M., et al., "Central Blood Pressure: Current Evidence and Clinical Importance," European Heart Journal 35(26):1719-1725, Jul. 2014.

Miyashita, H., "Clinical Assessment of Central Blood Pressure," Current Hypertension Reviews 8(2):80-90, May 2012.

Ogedegbe, G., and T. Pickering, "Principles and Techniques of Blood Pressure Measurement," Cardiology Clinic 28(4):571-586, Nov. 2010. (Author Manuscript provided, PMCID:PMC3639494, available in PMC Apr. 30, 2013, 26 pages.).

Pickering, T.G., et al., "Recommendations for Blood Pressure Measurement in Humans and Experimental Animals, Part 1: Blood Pressure Measurement in Humans," Circulation 111(5):697-716, Feb. 2005.

Raamat, R., et al., "Mathematical Modelling of Non-Invasive Oscillometric Finger Mean Blood Pressure Measurement by Maximum Oscillation Criterion," Medical & Biological Engineering & Computing 37(6):784-788, Nov. 1999.

Rosatella, G., et al., "Non Invasive Procedure to Evaluate the Viscoelastic Behavior of the Brachial Artery by Oscillometric Repeated Measurements," Proceedings of the 25th Annual International Conference of the IEEE EMBS, Cancun, Mexico, Sep. 17-21, 2003, pp. 3302-3305.

Schattenkerk, D.W.E., et al., "Nexfin Noninvasive Continuous Blood Pressure Validated Against Riva-Rocci/Korotkoff," American Journal of Hypertension 22(4):378-383, Apr. 2009.

Valentinuzzi, M.E., and A.J. Kohen, "Laplace's Law: What It Is About, Where It Comes From, and How It Is Often Applied in Physiology," IEEE Pulse 2(4):74-84, Jul.-Aug. 2011.

Van Bortel, L.M., et al., "Non-Invasive Assessment of Local Arterial Pulse Pressure: Comparison of Applanation Tonometry and Echo-Tracking," Journal of Hypertension 19(6):1037-1044, Jun. 2001.

Instructions for Use (IFU) for KardiaMobile 6L (AC-019), AliveCor, Nov. 2020, 19 pages.

KardiaMobile 6L, Portable 6-Lead EKG Device, AliveCor, Inc., https://store.alivecor.com/products/kardiamobile6l, Apr. 4, 2021, 9 pages.

\* cited by examiner

COMPREHENSIVE WEARABLE VITAL SIGNS MONITOR

CROSS-REFERENCE TO RELATED APPLICATIONS

The present application claims the benefit of U.S. Provisional Application No. 63/250,132, filed Sep. 29, 2021, the contents of which are hereby incorporated by reference.

TECHNICAL FIELD

This disclosure relates generally to vital signs monitoring, and in particular but not exclusively, relates to vital sign monitoring at a digital artery.

BACKGROUND INFORMATION

Accurate and timely vital sign monitoring is critical to obtaining positive patient health and clinical outcomes. Such monitoring enables early recognition of patient deterioration, which in turn facilities timely intervention. The five primary vital signs that medical professionals regularly check include: core temperature (normal body temperature for a healthy adult ranges between 97.8 F and 99 F), heart rate (normal resting heart rate for a healthy adult ranges between 60 and 100 bpm), blood pressure, respiratory rate, and oxygen saturation level (SpO2). A sixth useful signal is an electrocardiogram (ECG), which is a measure of electrical activity of the heart.

Constant monitoring in a hospital environment of these vital signs and signals is common. The hospital room is a conducive environment for regular acquisition and tracking of these vital signs. A wired pulse oximeter probe or photoplethysmography (PPG) sensor may be clipped onto a patient's fingertip to measure heart rate and SpO2 while also estimating respiratory rate. An oral thermometer may be periodically used to obtain the patients core temperature. A digital sphygmomanometer with an inflatable arm cuff may be continuously worn to acquire oscillometric measurements of systolic and diastolic blood pressure. Two to ten electrodes may be adhered to different parts of the patient's body to acquire ECG readings. These leads can include limb leads and chest leads. By combining electrical measurements (e.g., electrical potential across the patient's heart) across different combinations of the electrodes, various ECG readings can be acquired. A 12-lead ECG is acquired using measurements extracted from all ten electrodes. A 6-lead ECG is extracted from different combinations of the three limb electrodes forming points of what is known as Einthoven's triangle. A 1-lead ECG uses two electrodes, one coupled to each arm. Wearable watches currently available on the market are capable of obtaining a 1-lead ECG.

Acquiring and tracking these readings typically uses many different types of monitoring devices. While the multiple devices and integrated systems needed to gather and collate this data may be available in the hospital room environment, acquiring and tracking these five or six vital signs and signals can be complex and cumbersome outside of the hospital environment. A single, cost-effective device capable of conveniently acquiring and tracking these vital signs outside of the hospital environment would be desirable.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of operation for a wearable vital signs monitor are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Conventionally, to measure the five vital signs (heart rate, core body temperature, respiratory rate, blood oxygenation level, and blood pressure) along with obtaining an electrocardiogram (ECG), multiple different devices are required to be attached to multiple different locations on the body. Embodiments of the comprehensive vital signs monitor described herein are not only capable of measuring and monitoring all five vital signs plus obtaining ECGs, but do so in a single, compact, portable, finger wearable device. This finger wearable device is attractive in remote patient monitoring, telehealth, post-discharge, medication monitoring, and clinical trial applications due to its convenience, low cost, and comfort during extended periods or overnight use. The compact, comfortable nature of the finger wearable vital signs monitor is likely to result in higher patient compliance, providing improved data sets and patient monitoring. Not only can the vital signs monitor be worn throughout the day while the patient goes about his/her ordinary tasks, but it may also be worn at night to obtain vital signs monitoring while the patient is sleeping.

Figure 1A:
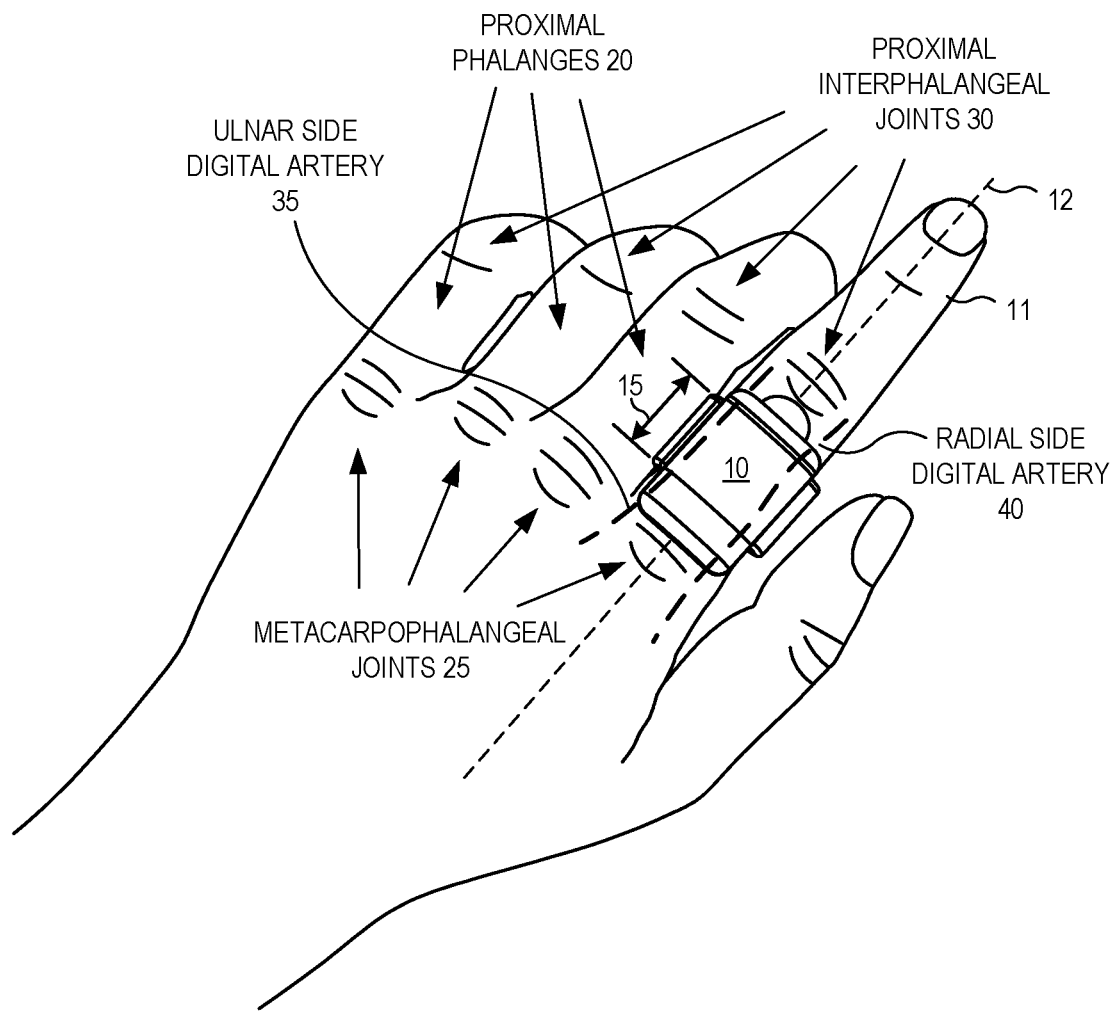
FIG. 1A is a perspective view illustration of finger wearable device for monitoring vital signs from a finger, in accordance with an embodiment of the disclosure.

FIG. 1A is a perspective view illustration of a wearable vital signs monitor 10 worn on a finger 11, in accordance with an embodiment of the disclosure. Vital signs monitor 10 is a non-intrusive, comprehensive way to measure and monitor the five vital signs plus ECGs of a wearer, though various embodiments may omit one or more vital sign sensors/ECG sensor.

FIG. 1A illustrates vital signs monitor 10 implemented as finger-wearable device; however, it is contemplated that vital signs monitor 10 may be implemented in other form factors and sizes for sliding over or wearing on other extremities or body parts. These extremities include, for example, wrists, upper arms, ankles, toes, or legs. Although FIG. 1A illustrates vital signs monitor 10 positioned over a left-hand index finger, it may be configured for use on a right-hand or on other fingers or thumbs of a user.

Vital signs monitor 10 attaches to the user's body part (e.g., finger 11) via a cuff having a size and shape for securing around the body part. In one embodiment, the cuff is fabricated of an inextensible material (e.g., nylon, plastic, metal, etc.) so that it doesn't stretch and dampen pulsatility signals before reaching the blood pressure (BP) sensor. The cuff cinches around a body part (illustrated as a finger cuff cinched around a finger) for occluding (or partially occluding) an artery within the body part. In one embodiment, the cuff may be manually cinched or automatically actuated via a motor, thereby reducing the cross-sectional area defined by the cuff. In other embodiments, a pump may be coupled to apply a preset pressure and expand an elastic membrane that extends across a BP sensing area (discussed below) to achieve actuation and occlusion of the artery. Of course, the cuff may be replaced with other types of body mounts having other form factors.

The illustrated embodiment of vital signs monitor 10 has a compact form factor with an axial width 15 of the cuff itself fitting over a proximal phalanx 20 of finger 11 between metacarpophalangeal joint 25 and proximal interphalangeal joint 30. This compact form factor provides the user freedom to bend and use finger 11 while wearing vital signs monitor 10, which lends itself well to longer term monitoring without significant user discomfort or disruption to daily activities. The configuration of vital signs monitor 10 illustrated in FIG. 1A obtains BP measurements from either or both of ulnar side digital artery 35 or radial side digital artery 40 running in finger 11. Of course, not all advantages or features need be present in all embodiments.

Figure 1B:
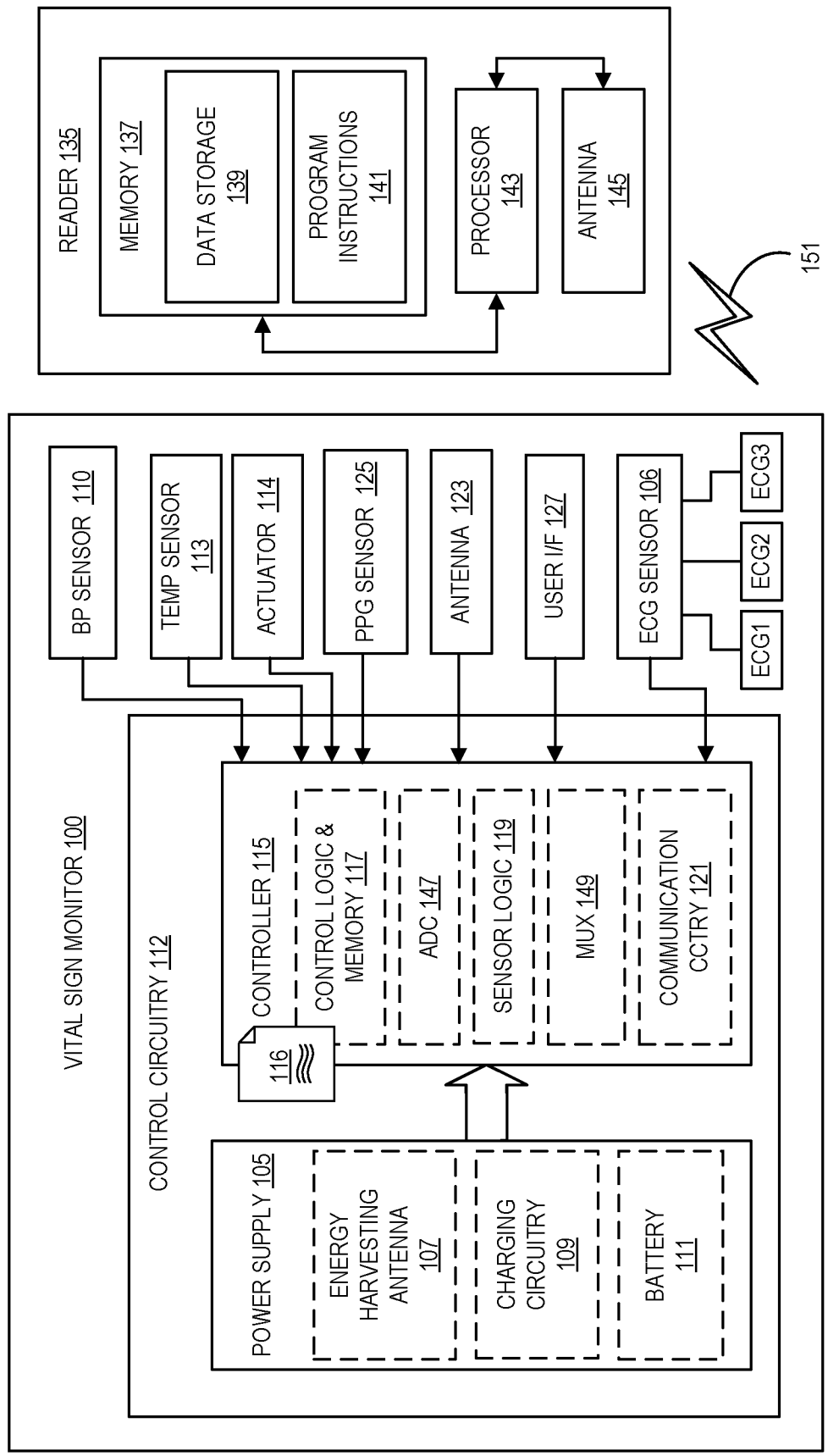
FIG. 1B is a functional block diagram illustrating functional components of a finger wearable device for monitoring vital signs, in accordance with an embodiment of the disclosure.

FIG. 1B is a functional block diagram illustrating functional electronic components of a finger wearable vital signs monitor 100, in accordance with an embodiment of the disclosure. Vital signs monitor 100 represents one possible implementation of vital signs monitor 10 illustrated in FIG. 1A. The illustrated embodiment of vital signs monitor 100 includes control circuitry 112, an ECG sensor 106 coupled to electrodes ECG1, ECG2, and ECG3, a BP sensor 110, a temperature sensor 113, an actuator 114, an antenna 123, photoplethysmogram (PPG) sensor 125, and user interface(s) 127. The illustrated embodiment of control circuitry 112 includes a power supply 105 and a controller 115. The illustrated embodiment of power supply 105 includes an energy harvesting antenna 107, charging circuitry 109, and a battery 111. The illustrated embodiment of controller 115 includes control logic and memory 117, sensor logic 119, Analog-to-Digital Converter (ADC) 147, a multiplexer (MUX) 149, and communication circuitry 121.

Power supply 105 supplies operating voltages to the controller 115 and various other sensors and components of vital signs monitor 100. In the illustrated embodiment, power supply 105 includes battery 111 to power the various embedded electronics, including controller 115. Battery 111 may be inductively charged by charging circuitry 109 and energy harvesting antenna 107. In one embodiment, antenna 123 and energy harvesting antenna 107 are independent antennae, which serve their respective functions of energy harvesting and communications. In another embodiment, energy harvesting antenna 107 and antenna 123 are the same physical antenna that are time shared for their respective functions of inductive charging and wireless communications with reader 135. In yet other embodiments, battery 111 may be charged via a wired port of vital signs monitor 100. Charging circuitry 109 may include a rectifier/regulator to condition the captured energy for charging battery 111 or directly power controller 115 without battery 111.

Controller 115 contains logic to choreograph the operation of the other embedded components. Control logic and memory 117 controls the general operation of vital signs monitor 100, including in some embodiments optionally providing a logical user interface, power control functionality, etc. Additionally, control logic and memory 117 may control the actuation of the finger cuff and receives and records the various vital sign signals from ECG sensor 106, BP sensor 110, temperature sensor 113, and PPG sensor 125. ADC 147 receives data from the sensors and converts any received analog data to a digital format and provides the same to control logic and memory 117 and/or sensor logic 119. In some embodiments, ADC 147 may be coupled to one or more of ECG sensor 106, BP sensor 110, temperature sensor 113, or PPG sensor 125 via MUX 149, which controls the inflow of data to the ADC 147. Vital signs monitor 100 may also include actuator 114 (e.g., cuff actuator, fluidic pump, etc.) that presses an interface surface of the vital signs monitor against the skin over an artery.

Sensor logic 119 includes the hardware/software logic for operation of the various vital sign sensors. In the case of BP sensor 110, sensor logic 119 receives the measurements (e.g., pulsatility signals or pressure measurements) from BP sensor 110 and converts the measurements into equivalent pressure values. The pressure values may be in mmHg, for example. The pressure values may further be converted into pressure waveforms that may be analyzed in either the time or frequency domains to determine mean arterial pressure, systolic blood pressure, and/or diastolic blood pressure at the digital artery. In some embodiments, the pulsatility signals may be converted from a first waveform type (e.g., pressure at the digital artery) to a second waveform type (e.g., pressure at a brachial artery). Sensor logic 119 may analyze the waveforms to identify arterial pulses and subsequently determine or estimate blood pressure. Vital signs monitor 100 may use a variety of techniques such as oscillometry, auscultation, or applanation tonometry to estimate a user's blood pressure at an artery in an extremity (e.g., digital artery of a finger), which may subsequently be converted to a clinical or brachial blood pressure with a transfer function and/or a machine learning algorithm.

For applanation tonometry, the finger cuff presses a BP sensing area into the body part over an artery, which may deform the artery. The artery may or may not be deformed to occlusion. As the pressure applied by the body part is slowly reduced, the artery may slowly convert back to a normal shape, and may pass through a point where the internal pressure equals the external pressure exerted on the artery by the BP sensing area. This point may occur when a local radius of the artery approaches infinity (i.e., flattens). In this state, e.g., with the local region of the artery being flat, the blood flow variations in the artery due to heart beats may cause the flat area of the artery to experience pressure fluctuations (e.g., arterial pulses). A maximum fluctuation, representing one of the arterial pulses having a pulse amplitude larger than the pulse amplitude of any other one of the arterial pulses, may occur at the flat condition. The pressure fluctuations may decrease when the local region is not quite flat. While the above operation was discussed in terms of a controlled reduction in pressure applied between a body part and the BP sensing area, the operation may alternatively be performed using a controlled increase in pressure and the pressure changes may be measured during the controlled increase.

In one embodiment, BP sensor 110 is operated to sense the above-mentioned pressure fluctuations or arterial pulses incident upon the BP sensing area of a semi-conformable bladder. An incompressible fluid is provided within the semi-conformable bladder to couple and propagate these pressure signals from the user's skin to the BP sensor 110. The pressure signals are sensed through a flexible membrane, which seals in the incompressible fluid and extends across the BP sensing area. The BP sensing area is then aligned over the artery to sense and propagate the pulsatility/pressure signals from the artery into the incompressible fluid. BP sensor 110 may be a waterproof sensor adapted for direct mechanical coupling to the incompressible fluid to measure the pulsatility/pressure signals. In another embodiment, a pressure sensor array (e.g., capacitive touch sensor array) may be positioned at the BP sensing area instead of using a semi-conformable bladder with a flexible membrane. In various embodiments, BP sensor 110 is designed, or low pass filtered, to focus on the lower frequencies (e.g., 0 to 20 Hz) generated by the human heart.

In some embodiments, BP sensor 110 may be a Korotkoff pressure sensor, and sensor logic 119 may receive sound recordings from BP sensor 110, which is essentially operating as a microphone to implement auscultatory blood pressure estimation. In one embodiment, BP sensor 110 is high pass filtered to extract the Korotkoff sounds. The Korotkoff sounds typically occur in frequency bands up to a few hundred hertz. Sensor logic 119 may analyze the sound recordings in relation to pressure data to determine a baseband pressure when Korotkoff sounds begin and end. If the pressure is decreasing during this time from an occluded state of the artery, the pressure corresponding to the beginning of the Korotkoff sounds may be an estimate of the systolic blood pressure, whereas the pressure corresponding to the ending of the Korotkoff sounds may be an estimate of the diastolic blood pressure.

In some embodiments, sensor logic 119 in concert with BP sensor 110 may determine the mean arterial pressure (MAP), systolic blood pressure (SBP), and diastolic blood pressure (DBP) using oscillometry. The determination of the mean arterial pressure, systolic blood pressure, and diastolic blood pressure may be similar to applanation tonometry techniques. For example, the pressure signals from BP sensor 110 may measure pressure changes due to blood flow in the digital artery. The pressure oscillations may start small, increase to a maximum amplitude, and reduce. Similar to the applanation tonometry technique, the applied pressure at maximum amplitude may be an estimate of the mean arterial pressure. From the measured pressure oscillations, sensor logic 119 may determine the mean arterial pressure, the systolic blood pressure, and the diastolic pressure. The systolic blood pressure and diastolic blood pressure can be calculated from the measured mean arterial pressure through one or more regressions (e.g., linear regression).

In some embodiments, sensor logic 119 may perform BP estimations using all three techniques. The BP estimations from the three different techniques can then be compared to determine a closest estimation of the user's BP at the peripheral artery in the extremity.

Sensor logic 119 may also include logic for analyzing the outputs from the other vital sign sensors. For example, sensor logic 119 may include the necessary logic for determining core body temperature from temperature sensor 113. Temperature sensor may be implemented as an infrared (IR) sensor, a thermocouple sensor, or both. Sensor logic 119 may further include logic for determining one or more of a heart rate, blood oxygenation level (SpO2), and respiratory rate from PPG sensor 125. In one embodiment, PPG sensor 125 is an optical pulse oximeter. Sensor logic 119 may further include logic for generating ECGs with the data output from ECG sensor 106. These ECGs may include 1-lead ECGs using electrical potential readings across the heart from electrodes ECG1 and ECG2 or 6-lead ECGs using electrical potential readings across the heart from all three electrodes ECG1, ECG2, and ECG3.

Control logic and memory 117 may gather and timestamp the various vital sign readings into a log 116 for short term storage prior to periodic uploads to reader 135 or cloud-based services. Control logic and memory 117 may further apply various analysis or thresholds to provide real-time feedback or issue real-time alarms to the user should any individual vital sign measurement (or combination of vital sign measurements) deviate outside of acceptable boundaries or ranges. The feedback/alarms may be audible and/or visual via user interface(s) 127. In one embodiment, vital signs monitor 100 may include an accelerometer so that control logic and memory 117 can reject certain readings acquired during high user motion events. Vital sign measurements obtained during high user motions may not be reliable. If accelerometer data shows that the body part was moving more than permissible during a blood pressure reading, control logic and memory 117 may reject that reading as unreliable.

Communication circuitry 121 provides communication protocols for wireless communication with reader 135 via antenna 123. In one embodiment, communication circuitry 121 provides backscatter communication via antenna 123 when in the presence of an electromagnetic field 151 output from reader 135. In one embodiment, communication circuitry 121 operates as a smart wireless radio-frequency identification ("RFID") tag that modulates the impedance of antenna 123 for backscatter wireless communications. The various logic modules of controller 115 may be implemented in software/firmware executed on a general purpose microprocessor, in hardware (e.g., application specific integrated circuit), or a combination of both. Of course, communication circuitry 121 and antenna 123 may implement other communication standards, such as WiFi, Bluetooth, etc.

The embodiment illustrated in FIG. 1B also includes reader 135 with a processor 143, an antenna 145, and memory 137. Memory 137 includes data storage 139 and program instructions 141. As shown, reader 135 may be disposed outside of device 100, but may be placed in its proximity to charge device 100, send instructions to device 100, and/or extract data from device 100. In one embodiment, reader 135 is a handheld portable device, such as a smartphone, a tablet, a laptop, or otherwise. In some embodiments, vital signs monitor 100 may communicate directly with cloud-based services using WiFi, or communicate indirectly with cloud-based services via reader 135. Reader 135 may execute an application that interfaces with vital signs monitor 100, provides feedback/diagnosis information to the user, implements a user interface, and/or extracts log 116 from vital signs monitor 100 and uploads it to cloud-based services. The cloud-based services, at the discretion of the patient, may conveniently provide the patient's vital signs data to their caregiver or doctor.

Figure 2A:
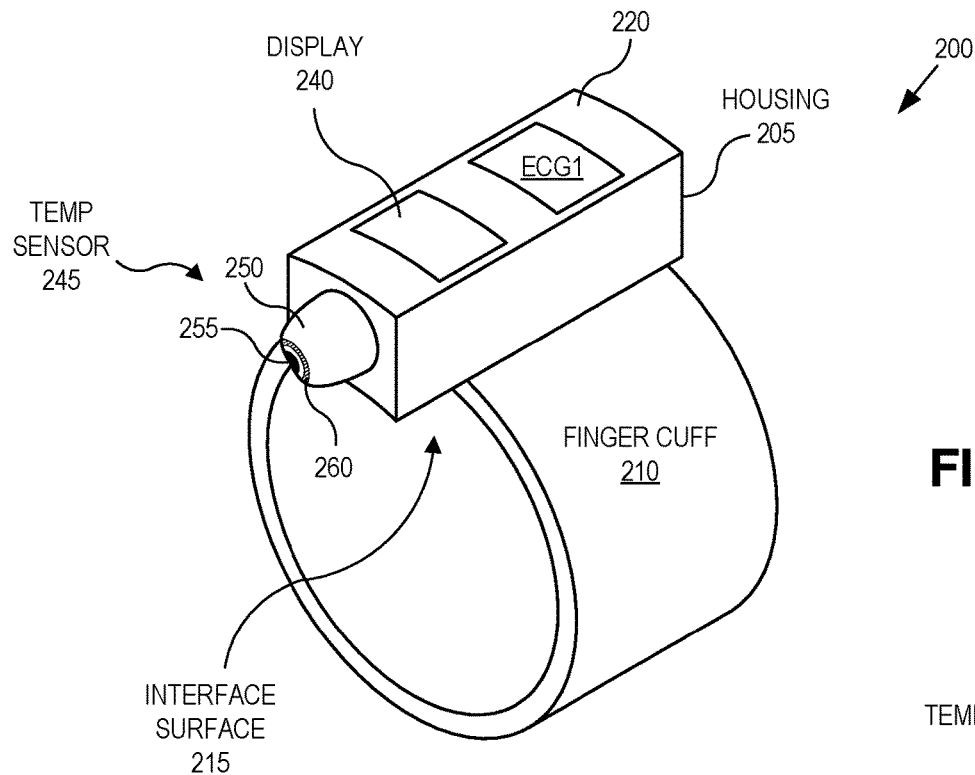
FIG. 2A is a top perspective view illustration of a finger wearable device for monitoring vital signs, in accordance with an embodiment of the disclosure.
Figure 2B:
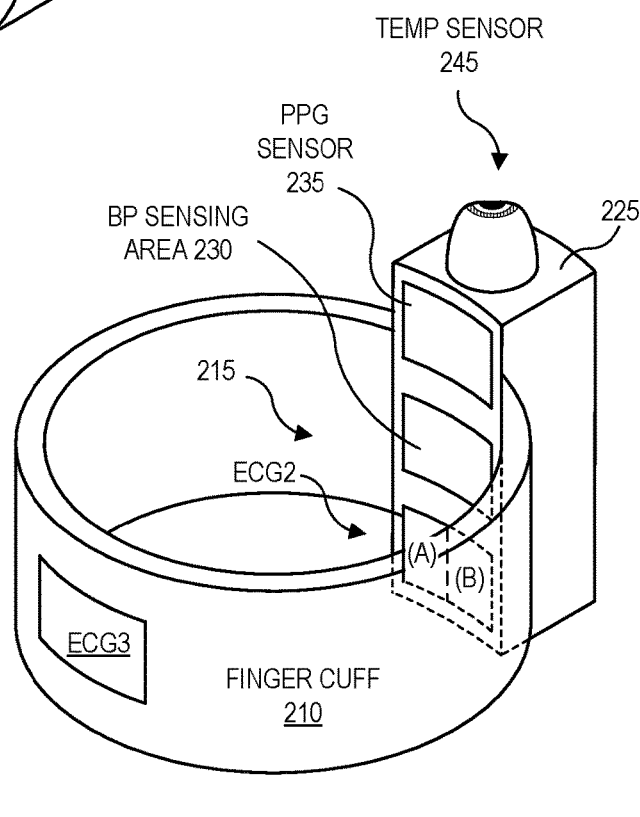
FIG. 2B is a bottom perspective view illustration of the finger wearable device for monitoring vital signs, in accordance with an embodiment of the disclosure.

FIGS. 2A and 2B illustrate a finger wearable vital signs monitor 200, in accordance with an embodiment of the disclosure. FIG. 2A is a top side perspective view illustration while FIG. 2B is a bottom side perspective view illustration of the same. Vital signs monitor 200 is one possible implementation and physical form factor of vital signs monitor 10 or 100. It should be appreciated that vital signs monitor 200 assumes a size and shape for wearing on a finger; however, the size and form factor may be adapted to wearing on a wrist, upper arm, angle, toe, or otherwise where an artery is sufficiently close to the skin surface to sense arterial pulses.

The illustrated embodiment of vital signs monitor 200 includes a housing 205 and a finger cuff 210. The illustrated embodiment of housing 205 includes an interface surface 215, a top surface 220, and a side 225. Interface surface 215 defines a BP sensing area 230 and further includes a PPG sensor 235 and electrode ECG2. Top surface 220 includes display (and/or other user interface) 240 and electrode ECG1. A temperature sensor 245 extends from side 225 of housing 205. The illustrated embodiment of temperature sensor 245 includes a protrusion 250 extending from side 225. Protrusion 250 may include one or both of a pointable infrared (IR) sensor 255 and/or ring-shaped thermocouple 260. The illustrated embodiment of finger cuff 210 includes an electrode ECG3 exposed on the outer surface of finger cuff 210.

Housing 205 includes the various sensors and electronics for measuring the user's vital signs. Finger cuff 210 attaches to housing 205 and squeezes, or otherwise forces, interface surface 215 of housing 205 against the extremity (e.g., finger). In addition to housing the various vital sign sensor electronics, housing 205 may also serve as a reservoir for containing an incompressible fluid (e.g., water, mineral oil, etc.). The incompressible fluid operates as the working fluid coupling the physiological pressure signals sensed at BP sensing area 230 to a pressure sensor that may be mounted in or on housing 205, or even remotely located via a hose that also contains the working fluid. BP sensing area 230 may be implemented as a hole or aperture in the rigid housing 205, which is sealed over with an elastic membrane material (e.g., nitrile, thermoplastic elastomers, etc.). Interface surface 215 is pressed against the extremity (e.g., finger), which in turn presses BP sensing area 230 against the skin in the vicinity of an artery to sense the arterial pulse signals. To improve the physical contact between BP sensing area 230 and the underlying extremity, interface surface 215 may be curved. In one embodiment, the radius of curvature substantially conforms to the underlying extremity (e.g., finger).

In some embodiments, the pressure/force by which BP sensing area 230 is pressed against the user's skin and underlying artery is dynamically adjusted by actuator 114 manipulated by controller 115. For example, the pressure/force of BP sensing area 230 against the underlying skin may be dynamically actuated or adjusted prior to each BP measurement under the influence of controller 115. This dynamic actuation may be achieved via a fluidic pump coupled to controller 115 that temporarily increases the pressure of the working fluid, thereby expanding the elastic membrane material against the skin over the artery and locally flattening the artery in the vicinity of BP sensing area 230. This localized flattening may be used to facilitate applanation tonometry, improve sensitivity for measuring BP pulsatility signals, etc. Alternatively, finger cuff 210 may be dynamically cinched (e.g., on-demand, periodically, etc.) for each BP measurement under the influence of controller 115. Cinching finger cuff 210 also achieves localized artery flattening under BP sensing area 230. The dynamic cinching of finger cuff 210 may be achieved using motors, pulleys, electroactive materials, or otherwise that are coupled to controller 115 and mechanically linked to finger cuff 210. In yet other embodiments, finger cuff 210 may apply a constant or static pressure to BP sensing area 230.

Figure 3:
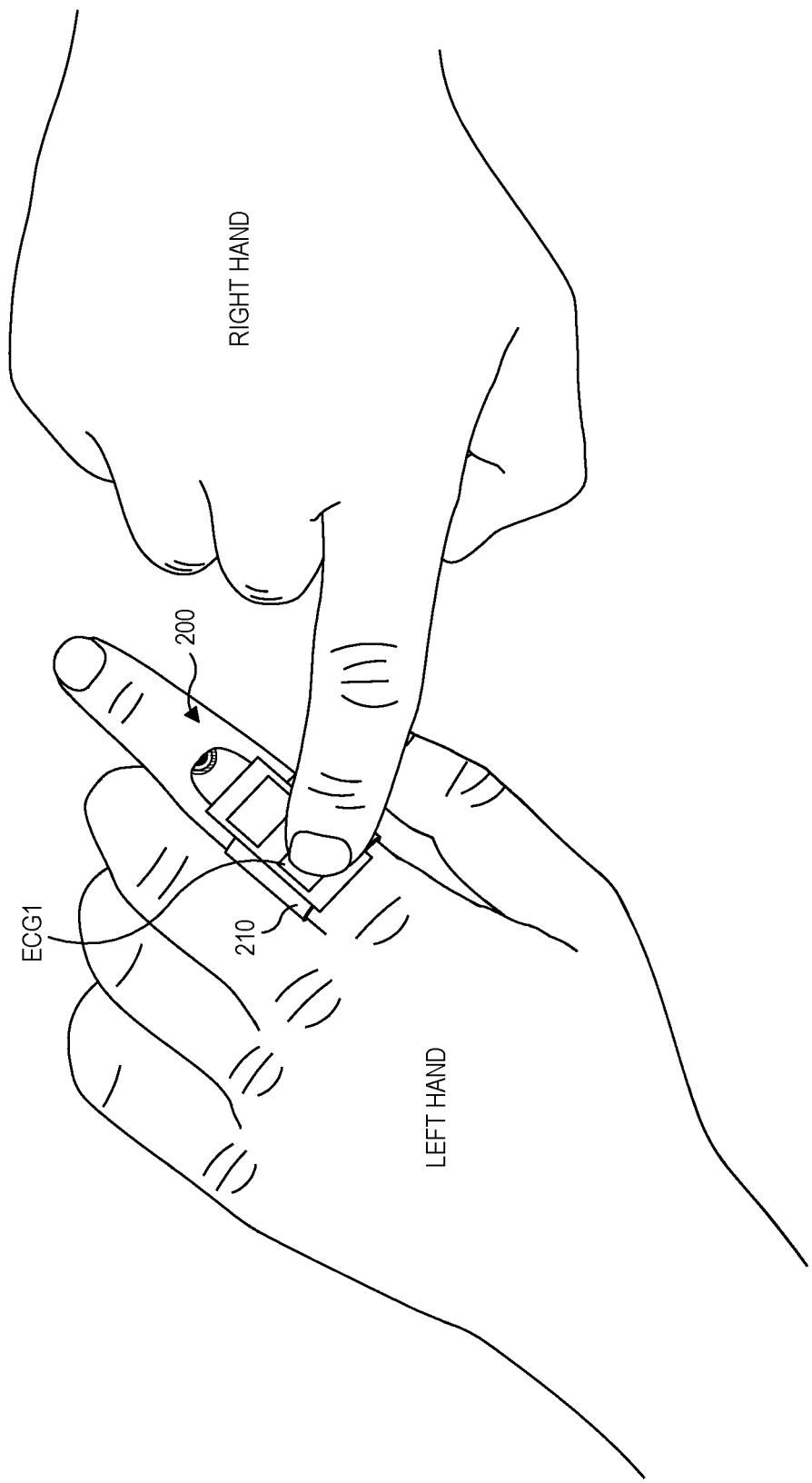
FIG. 3 illustrates how a wearer of the finger wearable device may obtain a 1-lead electrocardiogram (ECG) reading, in accordance with an embodiment of the disclosure.

In addition to BP sensing area 230, interface surface 215 includes electrode ECG2 disposed peripherally to BP sensing area 230. Electrode ECG2 is positioned to make electrical contact with the underlying extremity (e.g., finger). In contrast, electrode ECG1 is disposed on top surface 220, which is separate from, and oppositely disposed relative to, interface surface 215. This opposing configuration for electrodes ECG1 and ECG2, facilitates a user wearing vital signs monitor 200 on a finger of one hand while touching electrode ECG1 with a finger of the opposite hand. This setup facilitates a closed electrical connection between the user's right and left hands and enables acquiring a 1-lead ECG measuring electrical potential across the user's heart via electrodes ECG1 and ECG2. FIG. 3 illustrates a user taking a 1-lead ECG reading.

Referring to FIG. 2B, the illustrated embodiment of electrode ECG2 is subdivided into two parts: a first sub-electrode (A) and a second sub-electrode (B). These two sub-electrodes are positioned physically adjacent to each other on interface surface 215, but are otherwise insulated from each other. Electrode ECG2(B) provides common mode rejection of environmental electrical interference by driving back a subtractive excitation signal to cancel the body's electrical interference. The use of two sub-electrodes to implement electrode ECG2 is optional, but can improve ECG signal quality.

Figure 4:
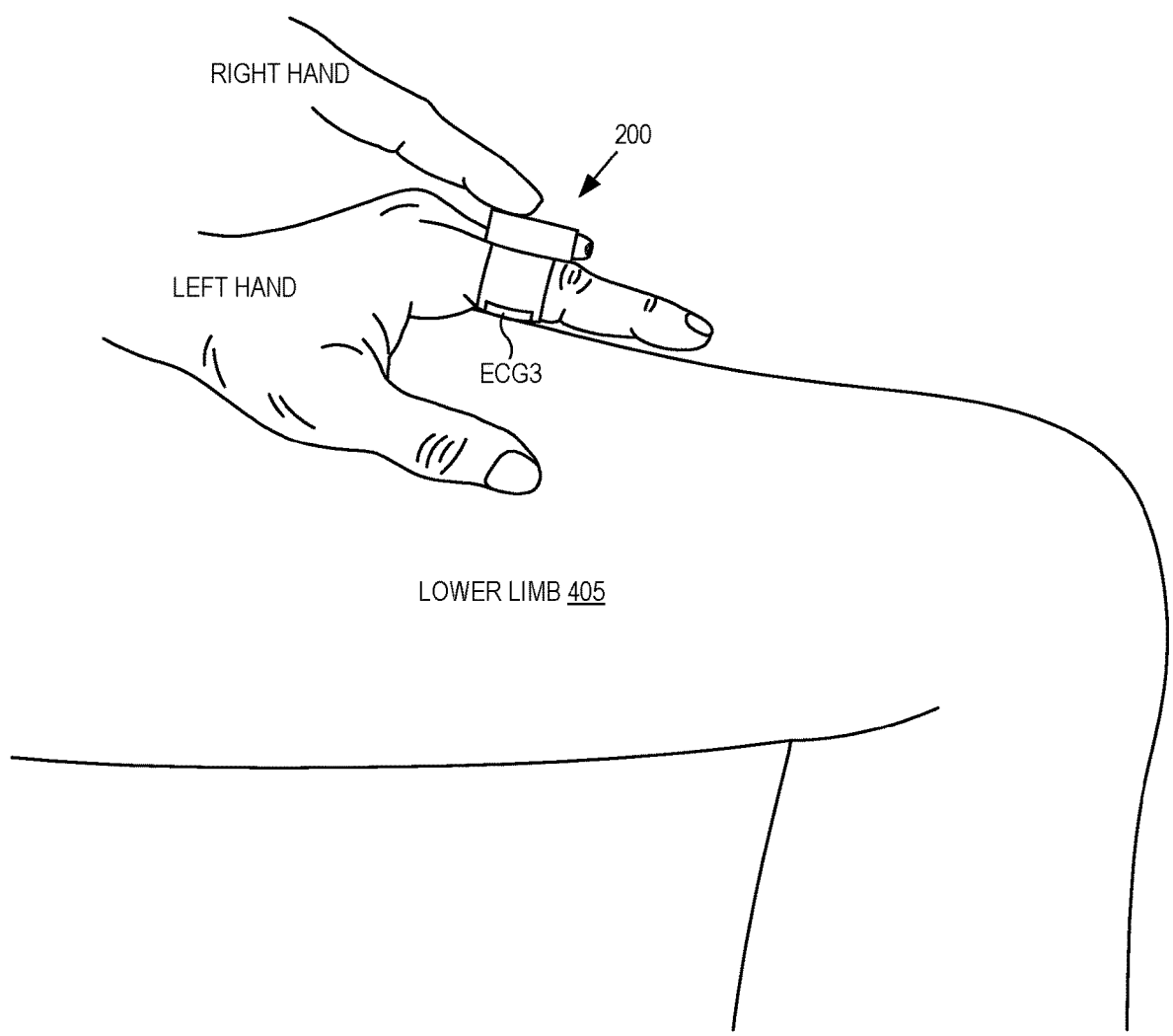
FIG. 4 illustrates how a wearer of the finger wearable device may obtain a 6-lead ECG reading, in accordance with an embodiment of the disclosure.

FIG. 2B further illustrates yet a third electrode ECG3 disposed on finger cuff 210. Electrode ECG3 is disposed on the out-facing side of finger cuff 210. In the illustrated embodiment, electrode ECG3 is disposed on the bottom, out-facing side of finger cuff 210. This position and orientation of electrode ECG3 relative to the other two electrodes ECG1 and ECG2 disposed on housing 205, facilitates 6-lead ECG readings by the wearer. FIG. 4 illustrates a user taking a 6-lead ECG reading with vital signs monitor 200. As illustrated, while the user wears vital signs monitor 200 on a first hand (e.g., finger of left hand), the user touches electrode ECG1 on the top surface 220 of housing 205 with the second hand (e.g., finger of right hand) while also touching electrode ECG3 on the underside of finger cuff 210 to a lower limb (e.g., thigh, shin, ankle, or foot). This three point touching configuration of all three electrodes ECG1, ECG2, and ECG3 enables simultaneous electrical contacts across the wearer's heart from three extremities, thereby enabling 6-lead ECG readings.

Returning to FIG. 2B, PPG sensor 235 is disposed within housing 205 to measure oxygen saturation levels, a pulse rate, and a respiratory rate from the user's finger via interface surface 215. In one embodiment, PPG sensor 235 is implemented as a pulse oximeter including one or more photodiodes to emit red and infrared light and a photodetector to measure light absorption at the different wavelength bands.

BP sensing area 230 is an active region covered by an elastic barrier material to measure small pulsatility signals propagating in an artery under the skin. BP measurements are improved when the skin surrounding BP sensing area 230 is stabilized and immobilized by pressing it against a rigid, static surface. Embodiments of vital signs monitor 200 leverage this stabilizing area by positioning other vital sign sensors with rigid, static components in this stabilizing area. In the illustrated embodiment, PPG sensor 235 and electrode ECG2 are both disposed along interface surface 215 peripheral to BP sensing area 230. PPG sensor 235 includes a rigid, transparent/translucent window on interface surface 215 while electrode ECG2 includes a rigid, conductive electrode(s) on interface surface 215. By centrally positioning BP sensing area 230 on interface surface 215 with electrode ECG2 and PPG sensor 235 peripherally disposed about BP sensing area 230, the useful stabilizing area of interface surface 215 is maximized thereby improving BP measurements while beneficially dedicating this area to other vital sign sensors to maintain a compact form factor.

Vital signs monitor 200 further includes a temperature sensor 245 disposed in or on housing 205 that is adapted for measuring core body temperature. In the illustrated embodiment, temperature sensor 245 includes a protrusion 250 that extends from side 225 of housing 205 and oriented for pointing at or pressing against a body part while wearing vital signs monitor 200 on a finger. The distal end of protrusion 250 may include a window for an IR sensor 255, a ring-shaped thermocouple 260, or both. The wear may point or press the distal end of protrusion 250 against a body cavity or body crevice that enables a core body temperature. Such areas may include an ear canal, an arm pit, or a mouth. Alternatively, the distal end of protrusion 250 may be pressed against the wearer's forehead.

Figure 5:
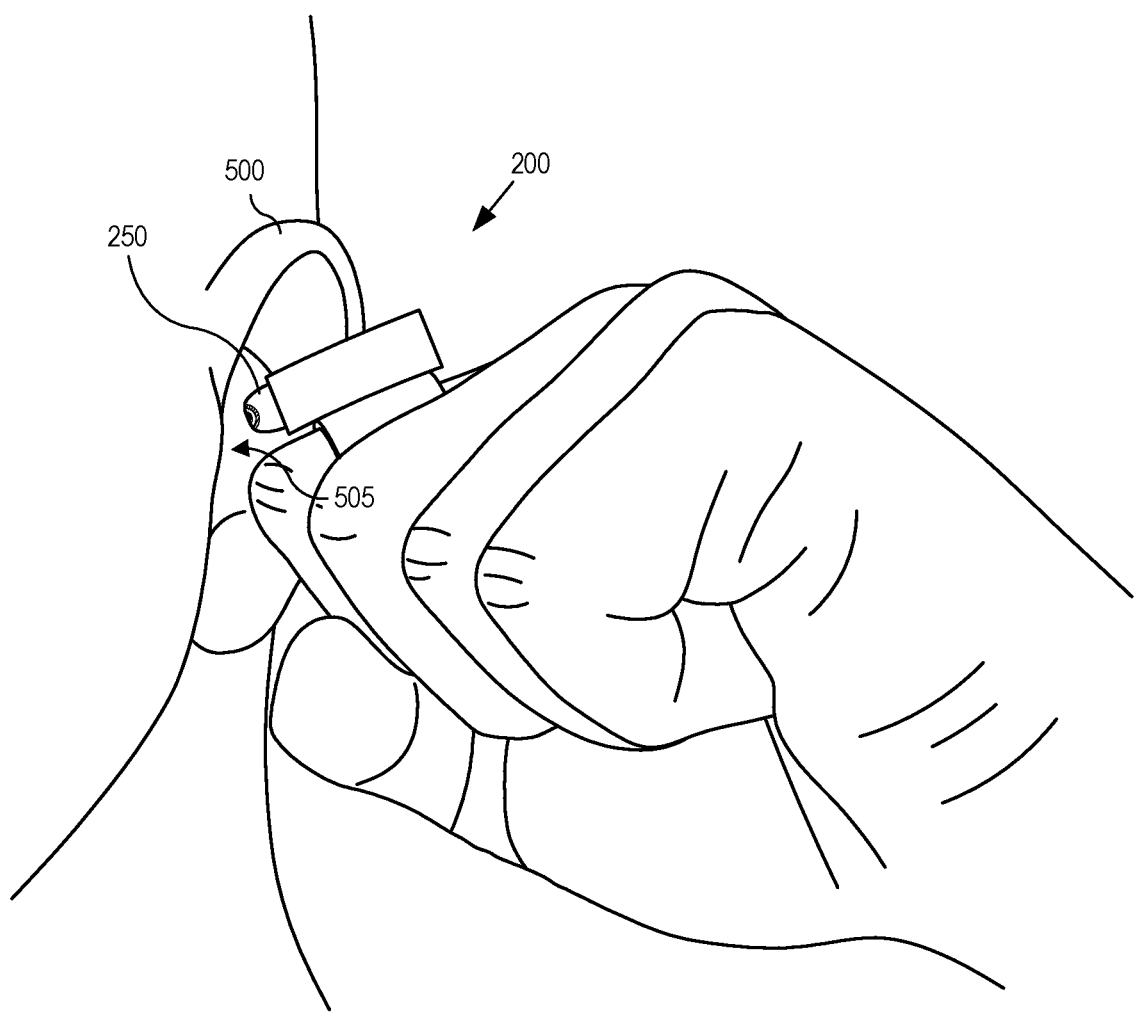
FIG. 5 illustrates how a wearer of the finger wearable device may measure a core body temperature with the finger wearable device, in accordance with an embodiment of the disclosure.

Protrusion 250 may provide multiple benefits for using temperature sensor 245. First, it provides the user with a physical element to align with or press against a body part and second it provides an offset from housing 205 to extend the distal end of temperature sensor 245 flush with or past the user's knuckle for embodiments that use physical contact with ring-shaped thermocouple 260. The ring-shape electrode of thermocouple 260 is particularly well suited for physically contacting the inner sides of the ear canal. As such, temperature sensor 245 may be configured for measuring core body temperature from the user's ear canal (see FIG. 5). In this embodiment, protrusion 250 is sized to place into ear 500 for alignment with ear canal 505. Protrusion 250 may help the user point and aim the IR temperature sensor, align and press the ring-shaped thermocouple 260, or both.

While the patient wears vital signs monitor 200, it may be operated to continually, periodically, or on-demand measure and record the user's vital signs. Controller 115 may operate to populate log 116 with the readings taken over a period of time (e.g., hours, days, weeks, etc.). The finger wearable form factor disclosed herein is small enough to wear throughout the day or overnight and may even be worn to obtain vital sign readings during specific events (e.g., sleeping, jogging, or other physical activities). As mentioned above, various embodiments may omit one or more of the sensors described and need not acquire all the vital signs described. For example, controller 115 may record four or more vital signs, all five vital signs, or even all five vital signs plus regularly acquire 1-lead and/or 6-lead ECG readings. Display 240 on top surface 220 may provide the user real-time feedback of their vital signs. Additionally, one or more user interfaces along with display 240 may facilitate various graphical interfaces, warnings, alarms, or other feedback/analysis. Controller 115 may periodically or on-demand export the vital signs data to reader 135 (e.g., user's mobile computing device) or upload the data to cloud-based services.

Some of the processes explained above may be described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A wearable device for monitoring vital signs at an extremity, the wearable device comprising:
    a housing including an interface surface for pressing against the extremity;
    a cuff attached to the housing and having a size and a shape to secure the housing to the extremity and force the interface surface against the extremity when the cuff is worn around the extremity;
    a plurality of vital sign sensors disposed in or on the housing and orientated to measure the vital signs from the extremity of a wearer of the wearable device; and
    an electrocardiogram (ECG) sensor disposed in or on the housing and coupled to first and second electrodes to measure ECG signals, wherein the second electrode is disposed on the interface surface,
    wherein the first electrode is disposed on a second surface of the housing different from the interface surface,
    wherein the second surface is opposite the interface surface,
    wherein the second electrode is subdivided into a first sub-electrode and a second sub-electrode for common mode rejection of electrical interference while measuring the ECG signals, wherein the first and second sub-electrodes are disposed on the interface surface and electrically insulated from each other.

2. The wearable device of claim 1, wherein the wearable device comprises a finger wearable device, the extremity comprises a finger, and the cuff comprises a finger cuff.

3. The wearable device of claim 2, further comprises:
a third electrode disposed on the finger cuff and coupled to the ECG sensor disposed within the housing.

4. The wearable device of claim 3, wherein the ECG sensor is configured to acquire 6-lead ECG readings of the wearer from the first, second, and third electrodes.

5. The wearable device of claim 3, wherein the finger comprises a first hand finger of the wearer and wherein the third electrode is positioned on the finger cuff such that the third electrode is pressable against a lower limb of the wearer while the first electrode is exposed for touching by a second hand finger of the wearer and the second electrode is pressed against the first hand finger.

6. The wearable device of claim 2, wherein the first and second sub-electrodes are disposed adjacent to each other on the interface surface.

7. The wearable device of claim 2, further comprising:
a controller disposed in or on the housing and coupled to the vital sign sensors and to the ECG sensor, the controller including logic that when executed by the controller causes the wearable device to perform operations including:
measuring the vital sign signals from the vital sign sensors from which four or more of the vital signs of the user are determinable; and
generating a log of the four or more vital signs.

8. A wearable device for monitoring vital signs at an extremity, the wearable device comprising:
a housing including an interface surface for pressing against the extremity;
a cuff attached to the housing and having a size and a shape to secure the housing to the extremity and force the interface surface against the extremity when the cuff is worn around the extremity;
a plurality of vital sign sensors disposed in or on the housing and orientated to measure the vital signs from the extremity of a wearer of the wearable device; and
an electrocardiogram (ECG) sensor disposed in or on the housing and coupled to first and second electrodes to measure ECG signals, wherein the second electrode is disposed on the interface surface,
wherein the vital sign sensors include:
a photoplethysmogram (PPG) sensor disposed to measure an oxygen saturation level, a pulse rate, and a respiratory rate from the extremity via the interface surface;
a blood pressure sensor disposed to measure a blood pressure of the wearer from the extremity via the interface surface; and
a temperature sensor configured to measure a core body temperature of the wearer.

9. The wearable device of claim 8, wherein the PPG sensor and the second electrode are peripherally disposed on the interface surface about a blood pressure sensing area for measuring the blood pressure.

10. The wearable device of claim 2, wherein the vital sign sensors include a temperature sensor disposed on a side of the housing and oriented for pointing at or pressing against a body part other than the finger while the wearable device is worn on the finger.

11. The wearable device of claim 10, wherein the temperature sensor comprises a core temperature sensor and is disposed in a protrusion extending from the side of the housing, wherein the protrusion is sized to place into an ear for aligning the core temperature sensor to an ear canal of the wearer.

12. The wearable device of claim 11, wherein the core temperature sensor comprises one or both of:
a pointable infrared sensor that is pointed from a distal end of the protrusion; or
a ring-shaped thermocouple that encircles the distal end of the protrusion.

13. The wearable device of claim 1, further comprising:
an actuator adapted to force the interface surface against the extremity; and
a controller coupled to the actuator to dynamically control the actuator.

14. A finger wearable device, comprising:
a housing;
a finger cuff attached to the housing and adapted to force the housing against a finger of a first hand of a wearer of the finger wearable device;
a plurality of vital sign sensors disposed in or on the housing and orientated to measure vital signs from the finger; and
an electrocardiogram (ECG) sensor disposed in or on the housing and coupled to first, second, and third electrodes to measure ECG signals, wherein the first and second electrodes are disposed on the housing with the second electrode positioned to contact the finger when the finger cuff is worn around the finger and the third electrode is disposed on the finger cuff and positioned for contacting a lower limb of the wearer while the first electrode is reachable by a second hand of the wearer.

15. The finger wearable device of claim 14, further comprising:
a controller disposed in or on the housing and coupled to the vital sign sensors and to the ECG sensor, the controller including logic that when executed by the controller causes the finger wearable device to perform operations including:
measuring vital sign signals from the vital sign sensors from which four or more vital signs of the wearer are determinable; and
generating a log of the four or more vital signs.

16. The finger wearable device of claim 15, wherein the vital sign sensors include:
a photoplethysmogram (PPG) sensor disposed to measure an oxygen saturation level and a pulse rate via the finger;
a blood pressure sensor disposed to measure a blood pressure of the wearer from the finger; and
a temperature sensor configured to measure a core body temperature of the wearer.

17. The finger wearable device of claim 16, wherein the PPG sensor and the second electrode are peripherally disposed on an interface surface of the housing about an active area for measuring the blood pressure at the finger.

18. The finger wearable device of claim 14, wherein the vital sign sensors include a temperature sensor disposed on a side of the housing and oriented for pointing at a body part while the finger wearable device is worn on the finger.

19. The finger wearable device of claim 18, wherein the temperature sensor comprises a core temperature sensor and is disposed in a protrusion extending from the side of the housing, wherein the protrusion is sized to place into an ear for aligning the core temperature sensor with an ear canal of the wearer.

20. The finger wearable device of claim 19, wherein the core temperature sensor comprises one or both of:
- a pointable infrared sensor that is pointed from a distal end of the protrusion; or
- a ring-shaped thermocouple that encircles the distal end of the protrusion.

21. A wearable device for monitoring vital signs at an extremity, the wearable device comprising:
- a housing including an interface surface for pressing against the extremity;
- a cuff attached to the housing and having a size and a shape to secure the housing to the extremity and force the interface surface against the extremity when the cuff is worn around the extremity;
- a plurality of vital sign sensors disposed in or on the housing and orientated to measure the vital signs from the extremity of a wearer of the wearable device; and
- an electrocardiogram (ECG) sensor disposed in or on the housing and coupled to first, second, and third electrodes to measure ECG signals, wherein the second electrode is disposed on the interface surface,
- wherein the third electrode is disposed on the cuff and coupled to the ECG sensor disposed within the housing,
- wherein the ECG sensor is configured to acquire 6-lead ECG readings of the wearer from the first, second, and third electrodes.

22. The wearable device of claim 21, wherein the first electrode is disposed on a second surface of the housing different from the interface surface.

23. A wearable device for monitoring vital signs at an extremity, the wearable device comprising:
- a housing including an interface surface for pressing against the extremity;
- a cuff attached to the housing and having a size and a shape to secure the housing to the extremity and force the interface surface against the extremity when the cuff is worn around the extremity;
- a plurality of vital sign sensors disposed in or on the housing and orientated to measure the vital signs from the extremity of a wearer of the wearable device; and
- an electrocardiogram (ECG) sensor disposed in or on the housing and coupled to first and second electrodes to measure ECG signals, wherein the second electrode is disposed on the interface surface,
- wherein the first electrode is disposed on a second surface of the housing different from the interface surface,
- wherein the second surface is opposite the interface surface,
- wherein the wearable device comprises a finger wearable device, the extremity comprises a finger, and the cuff comprises a finger cuff.

* * * * *